United States Patent
Anderheggen

(10) Patent No.: US 10,987,289 B2
(45) Date of Patent: Apr. 27, 2021

(54) AGENT FOR BLEACHING HAIR WITH AN INITIALLY RED OR RED-BLONDE HAIR COLOR

(71) Applicant: Henkel AG & Co. KGaA, Duesseldorf (DE)

(72) Inventor: Bernd Anderheggen, Moenchengladbach (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 638 days.

(21) Appl. No.: 15/576,704

(22) PCT Filed: May 13, 2016

(86) PCT No.: PCT/EP2016/060832
§ 371 (c)(1),
(2) Date: Nov. 23, 2017

(87) PCT Pub. No.: WO2016/188773
PCT Pub. Date: Dec. 1, 2016

(65) Prior Publication Data
US 2018/0133127 A1  May 17, 2018

(30) Foreign Application Priority Data
May 27, 2015 (DE) .................. 10 2015 209 739.0

(51) Int. Cl.
*A61Q 1/08* (2006.01)
*A61K 8/22* (2006.01)
*A61Q 5/08* (2006.01)
*A61K 8/38* (2006.01)

(52) U.S. Cl.
CPC ............. *A61K 8/22* (2013.01); *A61K 8/38* (2013.01); *A61Q 5/08* (2013.01); *A61K 2800/882* (2013.01)

(58) Field of Classification Search
None
See application file for complete search history.

(56) References Cited

U.S. PATENT DOCUMENTS

| | | | |
|---|---|---|---|
| 2003/0086882 A1* | 5/2003 | Schmenger | A61Q 5/08 424/62 |
| 2006/0269492 A1* | 11/2006 | Narasimhan | A61K 8/23 424/62 |
| 2008/0229512 A1* | 9/2008 | Syed | A61K 8/22 8/111 |
| 2011/0162671 A1* | 7/2011 | Gross | A61Q 5/08 132/208 |
| 2015/0238391 A1 | 8/2015 | Schoepgens et al. | |
| 2016/0058687 A1 | 3/2016 | Anderheggen et al. | |
| 2016/0058688 A1 | 3/2016 | Anderheggen et al. | |

FOREIGN PATENT DOCUMENTS

WO    2012025269 A2    3/2012

OTHER PUBLICATIONS

EPO, International Search Report and Written Opinion issued in International Application No. PCT/EP2016/060832, dated Jul. 28, 2016.

* cited by examiner

*Primary Examiner* — Jyothsna A Venkat
(74) *Attorney, Agent, or Firm* — Lorenz & Kopf, LLP

(57) ABSTRACT

A subject of the present disclosure is a cosmetic agent to lighten keratinous fibers containing—relative to its total weight—
(A) from about 12.0 to about 23.0 wt. % potassium peroxodisulfate and
(B) from about 10.0 to about 20.0 wt. % ammonium peroxodisulfate and
(C) from about 5.0 to about 15.0 wt. % sodium peroxodisulfate.
A second subject of the present disclosure is a method for lightening keratinous fibers, particularly red and/or reddish-blond keratinous fibers, wherein an agent of the first subject of the present disclosure is mixed with at least one additional component containing hydrogen peroxide and applied to the hair.

3 Claims, No Drawings

AGENT FOR BLEACHING HAIR WITH AN INITIALLY RED OR RED-BLONDE HAIR COLOR

CROSS-REFERENCE TO RELATED APPLICATION

This application is a U.S. National-Stage entry under 35 U.S.C. § 371 based on International Application No. PCT/EP2016/060832, filed May 13, 2016 which was published under PCT Article 21(2) and which claims priority to German Application No. 10 2015 209 739.0, filed May 27, 2015, which are all hereby incorporated in their entirety by reference.

TECHNICAL FIELD

The present disclosure is in the field of cosmetics and relates to agents for bleaching of keratinous fibers, particularly human hair. A second subject of the present disclosure is a method for bleaching hair, particularly hair with a red or red-blond initial color.

BACKGROUND

The bleaching of hair is based on oxidative destruction of the melanin pigments in the hair fiber. For a moderate bleaching effect, use of hydrogen peroxide is suitable—optionally with the use of ammonia or other alkalizing agents—as a sole oxidizing agent. A mixture of hydrogen peroxide and peroxodisulfate salts achieves a stronger bleaching effect.

In the case of a dark initial hair color, eumelanins (black melanin pigments) and pheomelanins (red melanin pigments) must be used, in the case of light or reddish hair, pheomelanins (red melanin pigments) are essentially degraded oxidatively. Eumelanins and pheomelanins are structurally different. Eumelanin is created due to enzymatic oxidation of DOPA, whereas pheomelanins are produced enzymatically from 5-cysteinyl-DOPA in a biosynthetic manner.

The pigment types differ in terms of their oxidation stability. In comparison with pheomelanins, eumelanines are more sensitive to oxidizing agents and are decomposed more quickly by them. By contrast, pheomelanins have a higher resistance to oxidizing agents and are decomposed more slowly and/or only incompletely.

With the bleaching of dark, i.e. dark-brown or black hair, therefore, the eumelanins are decomposed more quickly and/or to a greater extent in comparison with the pheomelanins, which often results in a reddening of the bleached hair.

Normally, such color shifts towards warmer, red to orange tones are undesired by the user. Therefore, this color shift is usually counteracted with shading or dyeing with the appropriate complementary color according to the theory of colors. In the process, the goal is a silvery-cooler impression of the bleaching result. A person skilled in the art refers to this as matting.

Therefore, to prevent reddening, matting dyes are often added to commercial bleaching agents. The matting dyes are blue or blue-gray dyes that can be partially oxidizing dye oxidative dye precursors. The matting dye has a complementary absorption for the pheomelanin remaining on the bleached hair and can thereby conceal the red color impression. However, use of the matting dye is also associated with various disadvantages. For example, the matting agents are often unstable in combination with the oxidizing agents and must be packaged separately. Furthermore, the matting agents can be washed out after repeated washing of the hair, so the reddening becomes more perceptible with each wash. Finally, use of the matting dye entails coloring, so that the entire lightening effect is diminished and a very light blond cannot be achieved in this manner.

When bleaching hair with a red-blond or red initial hair color, the pheomelanins responsible for the red hair coloring must be decomposed oxidatively as completely as possible. Due to the high resistance of pheomelanins to oxidizing agents, a significant lightening effect on red and/or reddish hair is difficult. In the case of reddish hair, in particular, incomplete bleaching leads to an unattractive, light-reddish color result, which does not provide an attractive result even when matting dyes are added.

Until now, no means have been known from the prior art, which allow strong bleaching without reddening and which lead to an attractive result in the bleaching of red or red blond hair.

The task of the present disclosure was to improve the properties of bleaching agents and to minimize the aforementioned disadvantages. In the process, the reddening that takes place during the bleaching of dark hair should, in particular, be minimized. The most complete bleaching possible and a complete decomposition of pheomelanins should be enabled during the bleaching of red hair.

BRIEF SUMMARY

Cosmetic agents and methods for their use are provided. In an exemplary embodiment, a cosmetic agent for lightening of keratinous fibers includes, relative to its total weight, components (A), (B), and (C). Component (A) is potassium peroxodisulfate present at from about 12.0 to about 23.0 wt. %, Component (B) is ammonium peroxodisulfate present at from about 10.0 to about 20.0 wt. %, and Component (C) is sodium peroxodisulfate present at from about 5.0 to about 15.0 wt %.

A method of using a cosmetic agent is provided in another embodiment. The method includes producing a ready-to-use agent for lightening of keratinous fibers by mixing a first component (K1) with a second component (K2). The agent is dispensed onto the keratinous fibers, and remains thereon for a period of from about 1 to about 60 minutes, and then the agent is washed out of the fibers. The first component (K1) includes, relative to its own weight, (A) from about 12.0 to about 23.0 wt % potassium peroxodisulfate, (B) from about 10.0 to about 20.0 wt. % ammonium peroxodisulfate, and (C) from about 5.0 to about 15.0 wt. % sodium peroxodisulfate. The second component (K2) is an oxidizing preparation that includes hydrogen peroxide.

A cosmetic agent is provided in another embodiment. The cosmetic agent includes (A) from about 12.0 to about 23.0 wt. % potassium peroxodisulfate, (B) from about 10.0 to about 20.0 wt. % ammonium peroxodisulfate, and (C) from about 5.0 to about 15.0 wt. % sodium peroxodisulfate. The weight ratio of (A) to (B) is from about 1.0 to about 1.2, the weight ratio of (A) to (C) is from about 1.6 to about 1.8, and the weight ratio of (B) to (C) is from about 1.4 to about 1.6.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Surprisingly, it was found that bleaching agents in which the three peroxodisulfate salts potassium peroxodisulfate, ammonium peroxodisulfate and sodium peroxodisulfate are used together in very specific weight ratios, is exemplified by outstanding bleaching with an especially good "red reduction", i.e. use of this bleaching agent produces clear and light blond tones without a red component.

A first subject of the present disclosure is a cosmetic agent to lighten keratinous fibers containing—relative to its total weight—

(A) from about 12.0 to about 23.0 wt. % potassium peroxodisulfate and (B) from about 10.0 to about 20.0 wt. % ammonium peroxodisulfate and (C) from about 5.0 to about 15.0 wt. % sodium peroxodisulfate.

The agent is a cosmetic agent, i.e. an agent that is suitable for use on the human head.

Accordingly, the first subject of the present disclosure is a cosmetic agent for the lightening of human hair, containing—relative to its total weight—

(A) from about 12.0 to about 23.0 wt. % potassium peroxodisulfate and (B) from about 10.0 to about 20.0 wt. % ammonium peroxodisulfate and (C) from about 5.0 to about 15.0 wt. % sodium peroxodisulfate.

Keratinous fibers include pelts, wool, feathers and, in particular, human hair. Although the contemplated agents are particularly suitable for lightening of keratinous fibers, there are no basic obstacles to their use in other fields.

The lightening of keratinous fibers is also understood to mean bleaching. Keratinous fibers can be measured by colorimetry (measurement of laboratory values). In the colorimetry system, the L-value denotes the lightness of a color and/or keratinous fiber (an L-value of 0 denotes black; with an L-value of 100, a diffuse white is present). If lightened hair is measured by colorimetry, it has a higher L-value than before the lightening.

As contemplated herein, the special component of potassium peroxodisulfate, ammonium peroxodisulfate and sodium peroxodisulfate is essential for the contemplated lightening agent. If all three peroxodisulfates are contained in specific, harmonized quantity ranges in the contemplated agents, an especially strong and clear lightening without reddening can be achieved. Red and red-blond keratinous fibers can also be lightened to an attractive blond with these agents.

The contemplated agents can also be, for example, solid, powdery or pasty agents that can be called booster powder, booster gel or booster paste due to their content of persulfates. These agents can be sold, for example, as a component of a kit (i.e. a multi-component package unit) and mixed with a second (or even a second and a third) component just before use. The second component is a liquid, gel or creamy formulation containing hydrogen peroxide.

The degree of reddening of the lightened keratinous fibers can be determined in colorimetric measurement of the keratinous fibers. In the colorimetry system (laboratory values), the a-value indicates the red and/or green portion of a color. A negative a-value denotes a color with a high proportion of green, whereas a positive a-value denotes a color with a high proportion of red. Therefore, a lightened strand with good red reduction has the lowest possible a-value.

The contemplated agent contains—relative to its total weight—from about 12.0 to about 23.0 wt. % potassium peroxodisulfate (A). Potassium peroxodisulfate is also referred to as potassium persulfate and has the empirical formula $K_2S_2O_8$.

The contemplated agent also contains—relative to its total weight—from about 10.0 to about 20.0 wt. % ammonium peroxodisulfate (B). Ammonium peroxodisulfate is also referred to as ammonium persulfate and has the empirical formula $(NH_4)_2S_2O_8$.

The contemplated agent also contains—relative to its total weight—from about 5.0 to about 15.0 wt. % sodium peroxodisulfate (B). Sodium peroxodisulfate is also referred to as sodium persulfate and has the empirical formula $Na_2S_2O_8$.

With selection of the optimal weight ratio of (A)/(B), i.e. of potassium peroxodisulfate (A) to ammonium peroxodisulfate (B), a color result with an especially low red portion can be achieved with the bleaching. It has been found that it is especially advantageous for minimization of the reddening if potassium peroxodisulfate is used in a quantity that is greater than or equal to the ammonium peroxodisulfate. It is particularly preferred if potassium peroxodisulfate is used in a slight to about 1.5-fold weight surplus. Therefore, it is particularly preferred if the weight ratio of potassium peroxodisulfate (A) to ammonium peroxodisulfate (B) has a value of from about 1.0 to about 1.5, preferably from about 1.0 to about 1.4, more preferably from about 1.0 to about 1.3 and particularly from about 1.0 to about 1.2.

In a particularly preferred embodiment, therefore, a contemplated cosmetic agent is exemplified in that the weight ratio of (A) to (B), i.e. the weight ratio (A)/(B), has a value of from about 1.0 to about 1.5, preferably from about 1.0 to about 1.4, more preferably from about 1.0 to about 1.3 and particularly from about 1.0 to about 1.2.

Example

If 100 g of a booster powder—in addition to other cosmetically acceptable components—contains (A) 17.0 wt. % potassium peroxodisulfate and (B) 15.0 wt. % ammonium peroxodisulfate, the weight ratio (A)/(B) is 1.13.

The weight ratio in which potassium peroxodisulfate (A) and sodium peroxodisulfate (C) are used together also has an influence on the minimization of reddening. In the process, especially good results were achieved when potassium peroxodisulfate (A) was used in a from about 1.3 to about 2.1 weight surplus in comparison with sodium peroxodisulfate (C).

In an additional particularly preferred embodiment, therefore, a contemplated cosmetic agent is exemplified in that the weight ratio of (A) to (C), i.e. the weight ratio (A)/(C), has a value of from about 1.3 to about 2.1, preferably from about 1.4 to about 2.0, more preferably from about 1.5 to about 1.9 and particularly from about 1.6 to about 1.8.

Example

If 100 g of a booster powder—in addition to other cosmetically acceptable components—contains (A) 17.0 wt. % potassium peroxodisulfate and (C) 10.0 wt. % sodium peroxodisulfate, the weight ratio (A)/(C) is 1.70.

Finally, the weight ratio in which ammonium peroxodisulfate (B) and sodium peroxodisulfate (C) are used together has an influence on the red portion of the bleached keratinous fibers. In this context, it has been found that especially clear blond tones could be achieved when ammonium peroxodisulfate (B) was used in a slight, preferably from about 1.1 to about 1.9-fold weight surplus in comparison with sodium peroxodisulfate (C).

In an additional particularly preferred embodiment, therefore, a contemplated cosmetic agent is exemplified in that the weight ratio of (B) to (C), i.e. the weight ratio (B)/(C), has a value of from about 1.1 to about 1.9, preferably from about 1.2-about 1.8, more preferably from about 1.3 to about 1.7 and particularly from about 1.4 to about 1.6.

Example

If 100 g of a booster powder—in addition to other cosmetically acceptable components—contains (B) 15.0 wt. % ammonium peroxodisulfate and (C) 10.0 wt. % sodium peroxodisulfate, the weight ratio (A)/(C) is 1.50.

As describe above, the contemplated agents contain—relative to their total weight—
(A) from about 12.0 to about 23.0 wt. % potassium peroxodisulfate and
(B) from about 10.0 to about 20.0 wt. % ammonium peroxodisulfate and
(C) from about 5.0 to about 15.0 wt. % sodium peroxodisulfate.

Therefore, the maximum portion of persulfates in the contemplated agent is about 58 wt. %. It is particularly preferable if the total content of all peroxodisulfates contained in the agent is from about 36.0 to about 48.0 wt. %, preferably from about 37.0 to about 47.0 wt. %, more preferably from about 38.0 to about 46.0 wt. % and particularly from about 39.0 to about 45.0 wt. %—relative to the total weight of the agent.

The total content of all peroxodisulfates contained in the agent is understood to mean the sum of potassium peroxodisulfate (A), ammonium peroxodisulfate (B) and sodium peroxodisulfate (C).

In another particularly preferred embodiment, therefore, a contemplated cosmetic agent is exemplified in that the total content of all peroxodisulfates (A)+(B)+(C) contained in the agent is from about 36.0 to about 48.0 wt. %, preferably from about 37.0 to about 47.0 wt. %, more preferably from about 38.0 to about 46.0 wt. % and particularly from about 39.0 to about 45.0 wt. %—relative to the total weight of the agent.

Example

If 100 g of a booster powder—in addition to other cosmetically acceptable components—contains (A) 17.0 wt. % potassium peroxodisulfate and (B) 15.0 wt. % ammonium peroxodisulfate and (C) 10.0 wt. % sodium peroxodisulfate, the total content of peroxodisulfates in the agent is 42.0 wt. %.

Potassium peroxodisulfate (A) can be contained in an amount of from about 12.0 to about 23.0 wt. % in the contemplated agent, wherein the quantity specified as a percentage is relative to the total weight of the agent. It is particularly preferred if potassium peroxodisulfate (A) is contained in a quantity of from about 13.0 to about 22.0 wt. %, preferably from about 14.0 to about 21.0 wt. %, more preferably from about 15.0 to about 20.0 wt. % and particularly from about 16.0 to about 19.0 wt. % in the lightening agent.

In another particularly preferred embodiment, therefore, a contemplated cosmetic agent contains—relative to its total weight—from about 13.0 to about 22.0 wt. %, preferably from about 14.0 to about 21.0 wt. %, more preferably from about 15.0 to about 20.0 wt. % and particularly from about 16.0 to about 19.0 wt. % potassium peroxodisulfate.

Ammonium peroxodisulfate (B) can be contained in an amount of from about 10.0 to about 20.0 wt. % in the contemplated agent, wherein the quantity specified as a percentage is relative to the total weight of the agent. It is particularly preferred if ammonium peroxodisulfate (B) is contained in a quantity of from about 11.0 to about 19.0 wt. %, preferably from about 12.0 to about 18.0 wt. %, more preferably from about 13.0 to about 17.0 wt. % and particularly from about 14.0 to about 16.0 wt. % in the lightening agent.

In another particularly preferred embodiment, therefore, a contemplated cosmetic agent contains—relative to its total weight—(B) from about 11.0 to about 19.0 wt. %, preferably from about 12.0 to about 18.0 wt. %, more preferably from about 13.0 to about 17.0 wt. % and particularly from about 14.0 to about 16.0 wt. % ammonium peroxodisulfate.

Sodium peroxodisulfate (B) can be contained in an amount of from about 5.0 to about 15.0 wt. % in the contemplated agent, wherein the quantity specified as a percentage is relative to the total weight of the agent. It is particularly preferred if sodium peroxodisulfate (B) is contained in a quantity of from about 6.0 to about 14.0 wt. %, preferably from about 7.0 to about 13.0 wt. %, more preferably from about 8.0 to about 12.0 wt. % and particularly from about 9.0 to about 11.0 wt. % in the lightening agent.

In another particularly preferred embodiment, therefore, a contemplated cosmetic agent contains—relative to its total weight—(B) from about 6.0 to about 14.0 wt. %, preferably from about 7.0 to about 13.0 wt. %, more preferably from about 8.0 to about 12.0 wt. % and particularly from about 9.0 to about 11.0 wt. % sodium peroxodisulfate.

The maximum portion of persulfates in the contemplated agent is about 58 wt. %. The remaining, at least about 42 wt. % of the agent is other cosmetically acceptable ingredients, such as carrier substances, alkalizing agents, care agents, thickening agents, surfactants, polymers, fats, oils or similar substances that the person skilled in the art can add to the agent to achieve the desired characteristics.

The contemplated agents can also contain one or multiple alkalizing agents. Suitable alkalizing agents are, for example ammonia, alkanolamines, basic amino acids, and inorganic alkalizing agents such as (earth) alkali metal hydroxides, (earth) alkali metal metasilicates, (earth) alkali metal phosphates and (earth) alkali metal hydrogen phosphates. Lithium, sodium, potassium and/or magnesium are preferred metal ions.

Inorganic alkalizing agents that can be used as contemplated herein are preferably selected from sodium hydroxide, potassium hydroxide, magnesium hydroxide, calcium hydroxide, barium hydroxide, sodium phosphate, potassium phosphate, sodium silicate, potassium silicate, magnesium silicate, sodium carbonate and potassium carbonate.

It has been found that use of metasilicates in the contemplated preparations is preferable. These enhance the bleaching effect while simultaneously reducing damage to the keratinous fibers. (Earth) Alkaline metal metasilicates are preferred here, particularly preferably alkali metal metasilicates and particularly sodium metasilicate have been found to be suitable. Therefore, preferred agents as contemplated herein contain—relative to their weight—from about 5 to about <10 wt. %, preferably from about 6 to about <9.5 wt. %, more preferably from about 6.5 to about <9 wt. %, particularly preferably from about 7 to about <8.5 wt. % and particularly from about 7.5 to about <8 wt. % (earth) alkaline metal metasilicates, preferably alkaline metal metasilicates and particularly sodium metasilicate.

Additional alkalizing agents which can be used as contemplated herein can also be selected from alkanolamines from primary, secondary or tertiary amines having a $C_2$-$C_6$-alkyl base body which bears at least one hydroxyl group. Particularly preferred alkanolamines are selected from the group formed from 2-aminoethan-1-ol (monoethanolamine), 3-aminopropan-1-ol, 4-amino-butan-1-ol, 5-aminopentan-1-ol, 1-aminopropan-2-ol (monoisopropanolamine), 1-aminobutan-2-ol, 1-aminopentan-2-ol, 1-aminopentan-3-ol, 1-aminopentan-4-ol, 2-amino-2-methyl-propanol, 2-amino-2-methylbutanol, 3-amino-2-methylpropan-1-ol, 1-amino-2-methylpropan-2-ol, 3-aminopropan-1,2-diol, 2-amino-2-methylpropan-1,3-diol, 2-amino-2-ethyl-1,3-propanediol, N,N-dimethyl-ethanolamine, triethanolamine, diethanolamine and triisopropanolamine. Particularly preferred alkanolamines are monoethanolamine, 2-amino-2-methyl-propanol and triethanolamine.

The basic amino acids which can be used as alkalizing agents as contemplated herein can be selected from the group which is formed from L-arginine, D-arginine, D/L-arginine, L-lysine, D-lysine, D/L-lysine, L-ornithine, D-ornithine, D/L-ornithine, L-histidine, D-histidine and/or D/L-histidine.

Particular preference is given to the use of at least one solid alkalizing agent from the group including of magnesium carbonate, magnesium hydrogen carbonate, magnesium hydroxide, calcium carbonate, calcium hydrogen carbonate, calcium hydroxide, ammonium carbonate, sodium carbonate, sodium bicarbonate, potassium carbonate and potassium bicarbonate, since the use of these alkalizing agents allows the preparation of the agent as contemplated herein as a solid, or pasty booster component while at the same time improving the bleaching performance.

In a further particularly preferred embodiment, a cosmetic agent as contemplated herein comprises one or more alkalizing agents from the group of magnesium carbonate, magnesium hydrogen carbonate, magnesium hydroxide, calcium carbonate, calcium hydrogen carbonate, calcium hydroxide, ammonium carbonate, sodium carbonate, sodium bicarbonate, potassium carbonate and potassium bicarbonate.

If the ready-to-use alkalizing agents contain mixtures, preferred contemplated preparations contain alkalizing agents in a quantity of from about 0.05 to about 20 wt. %, particularly from about 0.5 to about 10 wt. %, relative to the total weight of the agent in each case.

Particular preference is given to an agent which—relative to its total weight—contains from about 5.0 to about 20.0 wt. %, preferably from about 6.0 to about 17.5 wt. %, more preferably from about 7.0 to about 15.0 wt. % and particularly about 12.5 wt. % magnesium carbonate.

In another particularly preferred embodiment, therefore, a contemplated cosmetic agent contains—relative to its total weight—from about 5.0 to about 20.0 wt. %, preferably from about 6.0 to about 17.5 wt. %, more preferably from about 7.0 to about 15.0 wt. % and particularly from about 9.0 to about 12.5 wt. % magnesium carbonate.

In addition, the contemplated lightening agent also contains additional ingredients.

The agents as contemplated herein can additionally contain one or more fatty alcohols as consistency factors, which carry from about 6 to about 30 carbon atoms in their alkyl chain. The alkyl chain can contain one or multiple branches as cis- and/or trans-configured double compounds. Examples of this are hexyl alcohol (caproic alcohol), heptyl alcohol (enanthic alcohol), octyl alcohol (caprylic alcohol), nonyl alcohol (pelargonyl alcohol), undecyl alcohol, undec-10-en-1-ol, dodecyl alcohol (lauryl alcohol), 2,6,8-trimethyl-4-nonanol (iso-lauryl alcohol), tridecyl alcohol, tetradecyl alcohol (myristyl alcohol), pentadecyl alcohol, hexadecyl alcohol (cetyl alcohol, or palmityl alcohol), heptadecyl alcohol, octadecyl alcohol (stearyl alcohol), isostearyl alcohol, (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenyl alcohol), nonadecan-1-ol (nonadecalcohol), eicosan-1-ol (eicosyl alcohol/arachyl alcohol), (9Z)-eicos-9-en-1-ol (gadoleyl alcohol), (5Z,8Z,11Z,14Z)-eicosa-5,8,11,14-tetraen-1-ol (arachidonic alcohol)), heneeicosyl alcohol, docosyl alcohol (behenyl alcohol), (13Z)-docos-13-en-1-ol (erucyl alcohol)) or (13E)-docosen-1-ol (brassidyl alcohol). As contemplated herein, it is also possible to use mixtures of fatty alcohols which are obtained as such by purposeful mixture or by extraction methods. Examples are coconut alcohols (mixture of $C_8$-$C_{18}$-fatty alcohols) or cetearyl alcohol (1:1 mixture of $C_{16}$- and $C_{18}$-fatty alcohols).

Additional suitable nonionic ingredients are ethylene glycol ethers of fatty alcohols. Basically, ethylene glycol ethers of the aforementioned fatty alcohols can be used. For example, ethylene glycol ethers having a degree of ethoxylation of 1 (fatty alcohol monoethylene glycol ether), 2 (fatty alcohol diethylene glycol ether) or 3 (fatty alcohol triethylene glycol ether) are suitable. Preferred ethylene glycol ethers as contemplated herein are, for example laureth-1, laureth-2, laureth-3, isolaureth-1, isolaureth-2, isolaureth-3, trideceth-1, trideceth-2, trideceth-3, myreth-1, myreth-2, myreth-3, ceteth-1, ceteth-2, ceteth-3, steareth-1, steareth-2, steareth-3, oleth-1, oleth-2, oleth-3, ceteareth-1, ceteareth-2, ceteareth-3, coceth-1, coceth-2, cocoeth-3, pareth-1, pareth-2 and pareth-3. Particular preference is given to ceteth-1, laureth-2, ceteth-2, steareth-2, oleth-2, laureth-3, isolaureth-3, trideceth-3, ceteareth-3 and oleth-3.

Further suitable ingredients are addition products of fatty alcohols with propylene oxide. In principle, propylene glycol ethers of the aforementioned fatty alcohols can be used, wherein propylene glycol ethers with fatty alcohols having a low propylene degree of propylene are preferred. The degree of propylene is understood to mean the molar amount of propylene oxide that was used per mole of fatty alcohol. Propylene glycol ethers having a degree of propylene of from about 1 to about 3 are preferred. As contemplated herein, preferred ethylene glycol ethers are, for example, PPG-1 lauryl ether, PPG-2 lauryl ether, PPG-3 lauryl ether, PPG-1 isolauryl ether, PPG-1 tridecyl ether, PPG-2 tridecyl ether, PPG-3 tridecyl ether, PPG-2 myristylether, PPG-3 myristyl ether, PPG-1 cetyl ether, PPG-2 cetyl ether, PPG-3 cetyl ether, PPG-1 stearyl ether, PPG-2 stearyl ether, PPG-3 stearyl ether, PPG-1 oleyl ether, PPG-2 oleyl ether, PPG-3 oleyl ether, PPG-1 cetearyl ether, PPG-2 cetearyl ether, PPG-3 cetearyl ether, PPG-1 cocoyl ether, PPG-2 cocoyl ether and PPG-3 cocoyl ether. Particular preference is given to PPG-3 myristyl ether.

Fatty acid esters of polyhydric alcohols with saturated or unsaturated fatty acids having from about 8 to about 22, particularly from about 10 to about 18, carbon atoms in the fatty acid group can be used as suitable emulsifiers. Ethylene glycol, propylene glycol, glycerin, pentaerythrite, sorbitan or sugar, as well as homooligomers and heterooligomers are preferred polyhydric alcohols.

Esters of ethylene glycol or propylene glycol as contemplated herein are both the monofatty acid esters and the difatty acid esters with (poly-)ethylene and/or propylene glycols. Preferred fatty acids are, for example, lauric, myristic, palmitic, stearic, isostearic and oleic acid. Preferred compounds include ethylene glycol mono fatty acid esters, propylene glycol mono fatty acid esters, ethylene glycol difatty acid esters, polyethylene glycol mono-fatty acid esters and polyethylene glycol difatty acid esters. Compounds particularly preferred as contemplated herein are, for example, ethylene glycol distearate, ethylene glycol monostearate, propylene glycol monostearate, diethylene glycol monostearate, polyethylene glycol (100) monostearate, polyethylene glycol (200) monostearate, diethylene glycol monolaurate, polyethylene glycol (200) dilaurate, polyethylene glycol (100) monolaurate, polyethylene glycol (100) monooleate, polyethylene glycol (200) dioleate or polyethylene glycol (400) dioleate.

Mono-, di- or trifatty acid esters of glycerin, its oligomers or its addition products with ethylene oxide and/or propylene oxide are also suitable. Particular preference is given to glycerol mono-fatty acid esters, glycerol difatty acid esters and glycerol trifatty acid esters. Examples of this type of compound are glyceryl trilaurate, glyceryl tristearate, glyceryl tripalmitate, glyceryl tristearate, glyceryl triisostearate, glyceryl tristearate, glyceryl tricocoate, glyceryl dilaurate, glyceryl dimyristate, glyceryl dipalmitate, glyceryl distearate, glyceryl diisostearate, glyceryl dioleate, glyceryl dicocoate, glyceryl monolaurate, glyceryl monomyristate, glyceryl monopalmitate, glyceryl monostearate, glyceryl monoisostearate, glyceryl monooleate and glyceryl mono-cocoate. Furthermore, mono- or poly-fatty acid esters of triglycerides can also be used as contemplated herein. For this purpose, decaglycerol decoleate, decaglycerol octaoleate, decaglycerol decastearat, trigylceryl diisostearate or diglycerol monostearate are mentioned by way of example.

It is also possible to use triglycerides of hydroxy-group-carrying fatty acids, particularly castor oil, which can be used hardened or unhardened. Particular preference is given to ethoxylated castor oil.

Ingredients that are also suitable as contemplated herein are fatty acid esters of pentaerythritol, in particular pentaerythritol mono-fatty acid esters. Examples of these compounds are pentaerythritol mono-myristate, pentaerythritol monopalmitate, pentaerythritol monostearate and pentaerythritol monooleate.

Furthermore, the agents as contemplated herein can also contain one or more silicone oils, which can be selected, for example, from the group of cyclic silicone oils with the INCI designation cyclomethicone. The INCI designation cyclomethicone is understood to mean, in particular, cyclotri siloxane (hexamethylcyclotrisiloxane), cyclotetrasiloxane (octamethylcyclotetrasiloxane), cyclopentadienyl (decamethylcyclopentasiloxane) and cyclohexsiloxane (dodecamethylcyclohexsiloxane).

A suitable cyclomethicone substitute as contemplated herein is a mixture $C_{13}$-$C_{16}$-isoparaffins, $C_{12}$-$C_{14}$-isoparaffins and $C_{13}$-$C_{15}$-alkanes.

Additional suitable ingredients are also $C_8$-$C_{16}$-isoparaffins, particularly of isoparaffins, in particular of isononane, isodecane, isoundecane, isododecane, isotetradecane, isotetradecane, isopentadecane and isohexadecane, and mixtures thereof.

The aforementioned ingredients can be contained in the agent in a quantity of from about 0.1 to about 20.0 wt. %, relative to the total weight of the agent in each case.

Some of the aforementioned ingredients have proven to be particularly suitable, since they guarantee the physical and chemical stability of bleaching agents—if they are formulated in paste form—over long periods of time and are outstandingly compatible with the further ingredients as contemplated herein. Preferred agents as contemplated herein are exemplified in that they contain at least one hydrophobic ingredient from the group including of paraffin oil, polyisobutene, the alkyl benzoates, isopropyl palmitate, isohexadecane, isododecane and isononyl isononanoate.

The contemplated agents can also contain one or multiple polymers as an additional ingredient. Suitable examples are polymers or copolymers of ethylene/propylene/styrene and/or the copolymers of butylene/ethylene/styrene and/or the copolymers of butylene/propylene/styrene. The agents can also contain at least one natural polymer. Cellulose derivatives which are used as a thickening agent can be used as a natural polymer. Examples are agar-agar, carrageenan, alginates, xanthan gum, karaya gum, ghatti gum, tragacanth, scleroglucangium or gum arabic, alginates, pectins, polyoses, guar gums, locust bean flour, linseed gums, dextrans, pectins, staerke fractions and derivatives such as amylose, amylopectin and dextrins, gelatin and casein, and cellulose derivatives, such as, for example, methyl cellulose, carboxyalkyl celluloses such as carboxymethylcellulose and hydroxyalkyl celluloses such as hydroxyethyl cellulose.

Natural polymers from the indicated substance classes are commercially available and are available, for example, under the trade name Deuteron®-XG (anionic heteropolysaccharide based on β-d-glucose, d-mannose, d-glucuronic acid, Schoener GmbH), Deuteron®-XN (non-ionogenic polysaccharide, Schoener GmbH), Protanal RF 6650 alginates (sodium alginate, FMC biopolymer), Cekol (cellulose gum, Kelco), Kelzane (xanthan biopolymer, Kelco), Xanthan FN (xanthan biopolymer, Jungbunzlauer), Keltrol, e.g. Keltrol CG-T (xanthan biopolymer, Kelco) or Keltrol CG-SFT (xanthan biopolymer, Kelco).

In a further embodiment of the present disclosure, the contemplated agents contain xanthan. As contemplated herein, xanthans that are produced after the swelling of transparent preparations are preferred. Particular preference is given to the use of the xanthan biopolymer that are distributed under the trade name Keltrol CG-SFT by the company Kelco.

In a preferred embodiment, a contemplated agent contains from about 0.1 to about 5 wt. %, preferably from about 0.5 to about 4 wt. %, more preferably from about 1 to about 3 wt. %, even more preferably from about 1.25 to about 2.5 wt. % and particularly from about 1.5 to about 2 wt. % xanthan.

The compositions as contemplated herein can also contain at least one additional bleach booster which is different from the inorganic persalts.

Compounds which contain aliphatic peroxocarboxylic acids preferably having from about 1 to about 10 carbon atoms, in particular from about 2 to about 4 carbons atoms, under perhydrolysis conditions, and/or optionally substituted perbenzoic acid can be used as bleach boosters. Substances that have the 0- and/or N-acyl groups of the aforementioned number of carbon atoms and/or optionally substituted benzoyl groups are suitable substances. Preference is given to polyacylated alkylenediamines, particularly tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU), n-acylimides, in particular n-nonanoylsuccinimide (NOSI), acylated phenolsulfonates, in particular n-nonanoyl- or isononanoyloxybenzenesulfonate (n- or iso-NOBS), carboxylic anhydrides, in particular phthalic anhydride, acylated polyhydric alcohols, in particular triacetin, ethylene glycol diacetate and 2,5-diacetoxy-2,5-dihydrofuran.

The contemplated agents described above are persulfate-containing booster components which can be used in methods for lightening, particularly for bleaching of keratinous fibers.

The contemplated agent can be made available to the user or hairdresser in the form of a kit (a multi-component package unit) containing, in addition to the peroxodisulfates in a first component (K1) at least one additional component (K2) in an optimal manner. The second component (K2) is an oxidizing agent preparation with hydrogen peroxide. The oxidizing preparation (K2) is preferably available in liquid, cream or gel form. The two components (K1) and (K2) are mixed together shortly before application and the ready-to-use lightening agent is produced in this manner.

As contemplated herein, it is also possible that the components (K1), (K2) and additionally (K3) are mixed together to produce the ready-to-use lightening agent, wherein component (K3) can be a component that contains a care substance, a special alkalizing agent or one or multiple other ingredients not compatible with components (K1) and (K2).

A second subject of the present disclosure is a method for lightening keratinous fibers, including of the following steps in the specified sequence.

(i) production of a ready-to-use agent for lightening of keratinous fibers by mixing a first component (K1) with a second component (K2), (ii) dispensing of the ready-to-use agent onto the keratinous fibers, (iii) the agent remaining on the hair for a period of from about 1 to about 60 minutes and (iv) washing out the agent from the fibers, wherein the first component (K1) is an agent of the first subject of the present disclosure and the second component (K2) is an oxidizing preparation that contains hydrogen peroxide.

The ready-to-use agents are produced immediately before application on the hair by mixing the two preparations (K1) and (K2) and optionally a third preparation (K3) and/or additional preparations. With ready-to-use agents which are produced by mixing more than two preparations to form a finished application mixture, it may be insignificant whether two preparations are mixed together first and then the third preparation is added and mixed in or whether all preparations are combined and then mixed. The mixing can take place by stirring in a bowl or a cup or by shaking in a closable container.

Steps (i) and (ii) are carried out in immediate succession. In this connection, the term "immediate" is understood to mean a time period from a few seconds to about one hour, preferably up to about 30 minutes, particularly up to about 15 minutes.

The contemplated agents are applied in a method for lightening of keratinous fibers, particularly human hair, wherein the agent is applied to the keratinous fibers, left on the fibers at a temperature from room temperature up to about 45° C. for a dwell time of from about 1 to about 60 minutes and then rinsed out with water or washed out with shampoo.

The dwell time of the ready-to-use lightening agent can be from about 1 to about 60 minutes, preferably from about 15 to about 45 minutes, particularly from about 20 to about 40 minutes. It may be advantageous to support the lightening process with the addition of heat during the dwell time of the agent on the fibers. The addition of heat can take place with an external heat source, i.e. with the assistance of a hot air fan, as well as with the body temperature of the test person, particularly with hair lightening on the living test person. With the latter option, the portion to be lightened is normally covered with a hood. A dwell phase at room temperature is also the subject of the present disclosure. The temperature during the dwell time is preferably from about 20° C. to about 40° C., particularly from about 25° C. to about 38° C. The lightening agents provide good bleaching and lightening results with physiological compatible temperatures below about 40° C., in particular.

After the end of the dwell time, the lightening preparation is rinsed out of the hair with water or a cleaning agent. A commercially available shampoo, in particular, can be used as a cleaning agent, wherein the cleaning agent can be omitted and the rinsing process can take place with tap water if the lighten agent has a strong surfactant-containing carrier.

The ready-to-use lighting agents contain the peroxodisulfates described above in their specific quantity ratios and hydrogen peroxide and represents a reactive mixture which effectively oxidatively destroys the eumelanins and particularly the pheomelanins of the hair.

In order to obtain a ready-to-use lightening agent with an optimal composition, component (K1) and component (K2) are preferably mixed together in a specific mixture ratio. Preference is given to components (K1) and (K2) mixed in a mixture ratio (K1)/(K2) of from about 0.3 to about 1.0, preferably from about 0.3 to about 0.9, more preferably from about 0.3 to about 0.8 and particularly from about 0.3 to about 0.7. A mixture ratio of (K1)/(K2) of 1.0 means that a percentage by weight of the peroxodisulfate-containing component (K1) and a percentage by weight of the hydrogen-peroxide-containing preparation (K2) are mixed. A mixture ratio of (K1)/(K2) of 0.5 means that a percentage by weight of the peroxodisulfate-containing component (K1) and two percentages by weight of the hydrogen-peroxide-containing preparation (K2) are mixed.

A particularly preferred method is exemplified in that the first component (K1) and the second component (K2) are mixed together in a weight ratio (K1)/(K2) of from about 0.3 to about 1.0, preferably from about 0.3 to about 0.9, more preferably from about 0.3 to about 0.8 and particularly from about 0.3 to about 0.7.

The component (K2) is an oxidizing agent preparation containing hydrogen peroxide. In a preferred embodiment, hydrogen peroxide is used as an aqueous solution in the oxidizing agent preparation (K2). The concentration of a hydrogen peroxide solution in the dye preparation is determined by legal requirements and by the desired effect; preference is given to from about 1 to about 12 wt. % solutions in water.

Preferred preparations (K2) as contemplated herein are exemplified in that they contain from about 1.5 to about 12.0 wt. %, preferably from about 3.0 to about 11.0 wt. %, more preferably from about 4.5 to about 10.0 wt. % and particularly from about 5.5. to about 9.5 wt. % hydrogen peroxide, relative to the total weight of component (K2).

A particularly preferred method is exemplified in that the component (K2) contains from about 1.5 to about 12.0 wt. %, preferably from about 3.0 to about 11.0 wt. %, more preferably from about 4.5 to about 10.0 wt. % and particularly from about 5.5. to about 9.5 wt. % hydrogen peroxide, relative to the total weight of component (K2).

The component (K2) normally contains the hydrogen peroxide in a cosmetic carrier which is preferably aqueous, alcoholic or aqueous-alcoholic. Carriers such as creams, emulsions, gels or surfactant-containing, foaming solutions, such as shampoos, foaming aerosols, foam formulations or other preparations suitable for application on the hair, are used for treatment of the hair.

The component (K1) containing the peroxodisulfates and/or the oxidizing agent preparation (K2) can contain further bleach boosters in order to enhance the brightening effect, such as, for example, tetraacetylethylenediamine (TAED), 1,5-diacetyl-2,4-dioxohexahydro-1,3,5-triazine (DADHT), tetraacetylglycoluril (TAGU), n-nonanoylsuccinimide (NOSI), n-nonanoyl- or isononanoyloxybenzenesulfonate (n- or i-NOBS), phthalic anhydride, triacetin, ethylene glycol diacetate and 2,5-diacetoxy-2,5-dihydrofuran, and also carbonate salts or hydrogen carbonate salts, in particular ammonium hydrogen carbonate, ammonium carbonate, sodium bicarbonate, disodium carbonate, potassium bicarbonate, dipotassium carbonate and calcium carbonate, and nitrogen-containing, heterocyclic bleach boosters, such as 4-acetyl-1-methylpyridinium p-toluenesulfonate, 2-acetyl-1-methylpyridinium p-toluenesulfonate, and n-methyl-3,4-dihydroisoquinolinium p-toluenesulfonate.

To further enhance the lightening, at least one $SiO_2$-compound, such as silica or silicate, particularly sodium silicate can be added to the component (K1) and/or the component (K2). The SiO2-compound can be contained in the dye preparation (K1) and/or in the oxidizing agent preparation (K2). As contemplated herein, it can be preferable to use the SiO2-compounds in quantities of from about 0.05 wt. % to about 15 wt. %, more preferably in quantities of from about 0.15 wt. % to about 10 wt. % and particularly in quantities of from about 0.2 wt. % to about 5 wt. %, relative to the total weight of the dye preparation (K1) and/or the total weight of the oxidizing agent preparation (K2) in each case. The quantity specifications reflect the portion of $SiO_2$-compounds (without their water content) in the agents.

The components (K1) and/or (K2) can also contain additional active ingredients, adjuvants and additives in order to improve the dyeing and/or lightening effect and set further desired properties of the agent.

Preferably, the ready-to-use lightening agents are provided as a liquid preparation and, if appropriate, a further surface-active substance is added to the agents, wherein such surface-active substances are referred to as surfactants or emulsifiers depending on the field of application: They are preferably selected from anionic, zwitterionic, amphoteric and nonionic surfactants and emulsifiers.

Suitable, ready-to-apply agents as contemplated herein are exemplified in that the agent (i.e. the component (K1) and/or (K2)) also contains at least one anionic surfactant. Suitable anionic surfactants are fatty acids, alkyl sulfates, alkyl ether sulfates and ether carboxylic acids with 10 to 20 carbon atoms in the alkyl group and up to 16 glycol ether groups in the molecule.

Suitable, agents as contemplated herein are exemplified in that the agent (i.e. the component (K1) and/or (K2)) also contains at least one zwitterionic surfactant. Preferred zwitterionic surfactants are betaine, n-alkyl-n, n-dimethyl ammonioum-glycinate, n-acyl-aminopropyl-n,n-dimethyl ammonium glycinate, and 2-alkyl-3-carboxymethyl-3-hydroxyethyl-imidazoline. A preferred zwitterionic surfactant is known by the INCI designation cocamidopropyl betaine.

Suitable, agents as contemplated herein are also exemplified in that the agent (i.e. the component (K1) and/or (K2)) also contains at least one amphoteric surfactant. Preferred amphoteric surfactants are n-alkylglycines, n-alkylpropionic acids, n-alkylaminobutyric acids, n-alkyliminodipropionic acids, n-hydroxyethyl-n-alkylamidopropylglycines, n-alkyl-taurines, n-alkyl sarcosines, 2-alkylaminopropionic acids and alkylaminoacetic acids. Particularly preferred ampoteric surfactants are N-cocosalkylaminopropionate, cocosacylaminoethylaminopropionate and $C_{12}$-$C_{18}$ acylsarcosin.

It has also proved advantageous for the component (K2) to contain other, non-ionic surfactants. Preferred non-ionic surfactants are alkyl polyglycosides as well as alkylene oxide bound to fatty alcohols and fatty acids with from about 2 to about 30 moles of ethylene oxide per mole of fatty alcohol or fatty acid. Preparations with outstanding properties are also obtained if they contain fatty acid esters of ethoxylated glycerol as nonionic surfactants.

The nonionic, zwitterionic or amphoteric surfactants can be used in volumes from about 0.1 to about 45 wt. %, preferably from about 1 to about 30 wt. % and especially preferably from about 1 to about 15 wt. %, relative to the total quantity of component (K2).

The components (K1) and/or (K2) can also contain at least one thickening agent. There are essentially no limitations with respect to these thickening agents. Organic and purely inorganic thickening agents can be used.

Suitable thickening agents are anionic, synthetic polymers, cationic, synthetic polymers, naturally occurring thickening agents, such as nonionic guargums, scleroglucan, or xanthangum, arabic gum, ghatti gum, karaya gum, tragacanth gum, carrageenan gum, agar-agar, locust bean flour, pectins, alginates, starch fractions and derivatives such as amylose, amylopectin and dextrins, and cellulose derivatives, such as, for example, methyl cellulose, carboxyalkyl celluloses and hydroxyalkyl celluloses, non-ionic, fully synthetic polymers, such as polyvinyl alcohol or polyvinylpyrrolidinone; and inorganic thickening agents, in particular phyllosilicates such as, for example, bentonite, particularly smectites such as montmorillonite or hectorite.

It is also advantageous if the lightening agents (i.e. component (K1) and/or (K2)), if they contain hydrogen peroxide, contain at least one stabilizer or chelating agent. Particularly preferred stabilizers are phenacetin, alkali benzoates (sodium benzoate) and salicylic acid. Furthermore, all complexing agents of the prior art can be used. Preferred complexing agents as contemplated herein are nitrogen-containing polycarboxylic acids, in particular EDTA and EDDS, and phosphonates, in particular 1-hydroxyethane-1, 1-diphosphonate (HEDP) and/or ethylenediamine tetramethylene phosphonate (EDTMP) and/or diethylenetriamine pentamethylene phosphonate (DTPMP) or the sodium salts thereof.

Moreover, the contemplated agents can contain additional active ingredients, adjuvants and additives, such as nonionic polymers, such as vinylpyrrolidinon/vinylacrylat-copolymers, polyvinylpyrrolidinon, vinylpyrrolidinon/vinylacetat-copolymers, polyethylenglycols and polysiloxanes; additional silicones such as volatile or non-volatile, straight-chained, branched or cyclical, cross-linked or non-cross-linked polyalkylsiloxanes (such as dimethicones or cyclomethicones), polyarylsiloxanes and/or polyalkylarylsiloxanes, more particularly polysiloxanes with organofunctional groups such as substituted or unsubstituted amines (amodimethicones), carboxyl-, alkoxy- and/or hydroxyl groups (dimethiconcopolyols), lineare polysiloxan(A)-polyoxyalkylen(B)-block copolymers, grafted silicon polymers; cationic polymers such as quaternized cellulose ether, polysiloxanes with quaternary groups, dimethyldiallylammoniumchlorid-polymers, acrylamid-dimethyldiallyl-ammonium chloride copolymers, with diethylsulfate quaternated dimethylamino-ethylmethacrylat-vinylpyrrolidinon-copolymers, vinylpyrrolidinon-imidazolinium-methchlorid-copolymers and quaternated polyvinylalcohol; zwitterionic and amphoteric polymers; anionic polymers such as polyacryl acids or cross-linked polyacryl acids; structurants, such as glucose, malic acid and lactic acid, hair-conditioning compounds such as phospholipides, for example lecithin and kephaline; perfume oils, dimethylisosorbid and cyclodextrine; fiber structure-improving agents, more particularly mono-, di- and oligosaccharides, such as glucose, galactose, fructose, fruit sugar and lactose; dyes for coloring the preparations; anti-dandruff active ingredients such as piroctone olamine, zinc omadine and climbazol; amino acids and oligopeptides; protein hydrolysates on an animal and/or plant basis, as well as in the form of their fatty acid condensation products or, where applicable, anionically or cationically modified derivatives; plant oils; light stabilizers and UV blockers; active ingredients such as panthenol, pantothenic acid, pantolacton, allantoin, pyrrolidinoncarbonic acids and the salts thereof, as well as bisabolol; polyphenols, more particularly hydroxy cinnamic acids, 6,7-dihydroxycumarines, hydroxybenzoic acids, catechins, tannins, Leukoanthocyanidine, anthocyanidines, flavanons, flavons and flavonols; ceramides or pseudoceramides; vitamins, provitamins and vitamin precursors; plant extracts; fats and waxes such as fatty alcohols, beeswax, montan wax and paraffins; source and penetration substances such as glycerin, propylene glycolmonoethylether, carbonate, hydrogen carbonate, guanidine, urea, as well as primary, secondary and tertiary phosphates; opacifiers such as latex, styrene/PVP and styrene/acrylamide copolymers; pearl shine concentrates such as ethylenglycolmono- and -distearate as well as PEG-3-distearate; pigments as well as propellants such as propane-butane-mixtures, $N_2O$, dimethylether, $CO_2$ and air.

The person skilled in the art will select these other substances in accordance with the desired properties of the agent. With regard to further optional components and the amounts of these components used, reference is expressly made to the relevant handbooks known to the person skilled in the art. In the agents as contemplated herein, the additional active ingredients and excipients are preferably used in quantities of from about 0.0001 to about 25 wt. %, particularly from about 0.0005 to about 15 wt. %, relative to the total weight of the component (K1) and/or the oxidant preparation (K2).

As describe above, the contemplated method is very well-suited for lightening and bleaching of dark hair, wherein a strong lightening with simultaneous minimization of reddening can be observed.

The special combination of three peroxodisulfates: potassium peroxodisulfate, ammonium peroxodisulfate and sodium peroxodisulfate, is capable of effectively oxidatively destroying the pheomelanin pigments contained in the hair. For this reason, the contemplated method is also particularly well-suited for bleaching hair with a red and reddish blond initial color and achieves a consistent, strong bleaching with attractive color result and minimized portion of red even with this initial hair color.

In a further explicitly preferred embodiment, a contemplated method is a method for lightening red or red-blond hair.

In a further explicitly preferred embodiment, a contemplated method is exemplified in that the
(i) application of the ready-to-use agent on the hair takes place with a high proportion of pheomelanin.

Hair with a high portion of pheomelanin is understood to mean a red to blond-red initial hair color.

In a further explicitly preferred embodiment, a contemplated method is exemplified in that the (ii) Application of the read-to-apply agent takes place on hair having a red to blond-red initial color.

The preferred embodiments of the first subject of the present disclosure also apply mutatis mutands for the second subject of the present disclosure.

EXAMPLES

The following formulations were created (all data in wt. %)

| Component (K1) | (E) As contemplated herein | (V) Comparison |
|---|---|---|
| Britesil C 265 | 36.0 | 36.0 |
| Magnesium carbonate | 9.65 | 9.65 |
| Sodium hexametaphosphate | 0.20 | 0.20 |
| Rohagit S hv | 1.00 | 1.00 |
| EDTA | 2.00 | 2.00 |
| Silica | 0.4 | 0.4 |
| Glycin | 0.6 | 0.6 |
| Cekol 50000 | 2.0 | 2.0 |
| Potassium persulfate | 17.00 | 32.00 |
| Ammonium persulfate | 15.00 | 10.00 |
| Sodium persulfate | 10.00 | — |
| Ariabel Blue 300302 | 0.15 | 0.15 |
| Dimethicone, dimethiconol | 1.50 | 1.50 |
| Paraffinum Liquidum | ad 100 | ad 100 |

| Component (K2) | Oxidant preparation (OX) |
|---|---|
| Emulgade F | 4.0 |
| Potassium hydroxide | 0.1 |
| Sodium benzoate | 0.1 |
| Dinatrium pyrophosphate | 0.1 |
| Dipicolinic acid | 0.1 |
| Etidronic acid (60% aqueous solution) | 0.3 |
| Paraffinum liquidum | 17.0 |
| Hydrogen peroxide (50% hydrous solution) | 18.2 |
| Water | ad 100 |

Raw materials used:
Britesil C 265: Sodium silicate, proportion of $SiO_2$: from about 57.0-about 59.9 wt. %, proportion of $Na_2O$: from about 21.3-about 22.8 wt. %,
Molar ratio of $SiO_2/Na_2O=2.65$
Rohagit S hv: Methyl methacrylate, methacrylic acid copolymer (Evonik)
Cekol 50000: Carboxymethylcellulose, sodium salt (cellulose gum) (CP Kelco, Nordmann Rassmann)
Ariabel Blue 300302: CI 77007 (ULTRAMARINES)
Emulgade F: Cetearyl alcohol, PEG-40 Castor Oil, sodium cetearyl sulfate (BASF)

Formulations (E) and (OX) were mixed together in a weight ratio of 1:2 (1 percentage by weight of formulation (E) and 2 percentages by weight of formulation (OX)).

Formulations (V) and (OX) were mixed together in a weight ratio of 1:2 (1 percentage by weight of formulation (V) and 2 percentages by weight of formulation (OX)).

Hair strands were measured by employing colorimetry prior to the bleaching. Then both ready-to-apply lightening agents (E+OX and V+OX) were applied to hair strands and left in place for 45 minutes at 35° C. in a drying cabinet. Then the hair strands were cleaned with a shampoo, rinsed with water and then dried. The hair strands were measured again by employing colorimetry after the drying.

The color distance (ΔE value) between the untreated and the bleached hair was determined from the obtained laboratory values.

Colorimetric Values

|  | L | a | b | ΔE |
|---|---|---|---|---|
| Untreated | 18.14 | 1.87 | 1.85 | — |
| Bleached with V + OX | 50.09 | 12.03 | 32.96 | 45.74 |
| Bleached with E + OX | 53.01 | 11.44 | 33.12 | 47.81 |

The higher the L-value, the better the lightening result.

The lower the a-value, the lower the reddening of the hair strands.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic agent for lightening hair consisting of—relative to its total weight—
(A) 17 wt. % potassium peroxodisulfate;
(B) 15 wt. % ammonium peroxo disulfate
(C) 10 wt. % sodium peroxodisulfate;
sodium silicate;
magnesium carbonate;
sodium hexametaphosphate;
methyl methacrylate, methacrylic acid copolymer;
ethylene diamine tetra acetic acid (EDTA);
silica;
glycine;
a sodium salt of carboxymethylcellulose;
dye;
dimethicone and dimethiconol; and
paraffinum liquidum.

2. A method for lightening hair comprising the following steps in the specified sequence
(i) producing a ready-to-use agent for lightening of keratinous fibers by mixing a first component (K1) with a second component (K2),
(ii) dispensing of the ready-to-use agent onto the keratinous fibers,
(iii) the agent remaining on the hair for a period of 1 to 60 minutes and
(iv) washing out the agent from the fibers,
wherein
the first component (K1) is cosmetic agent according to claim 1; and
the second component (K2) is an oxidizing preparation that comprises hydrogen peroxide.

3. The method according to claim 2 wherein the hair is red or red-blond hair.

* * * * *